(12) United States Patent
Miller

(10) Patent No.: US 11,116,664 B2
(45) Date of Patent: Sep. 14, 2021

(54) MONITOR EFFICACY OF LASER EYE TREATMENT THROUGH CELL LYSIS DETERMINATION

(71) Applicant: LUTRONIC VISION INC., Burlington, MA (US)

(72) Inventor: Seth Adrian Miller, Longmont, CO (US)

(73) Assignee: LUTRONIC VISION INC., Burlington, MA (US)

(*) Notice: Subject to any disclaimer, the term of this patent is extended or adjusted under 35 U.S.C. 154(b) by 0 days.

(21) Appl. No.: 16/765,128

(22) PCT Filed: Nov. 30, 2017

(86) PCT No.: PCT/US2017/063845
§ 371 (c)(1),
(2) Date: May 18, 2020

(87) PCT Pub. No.: WO2019/108189
PCT Pub. Date: Jun. 6, 2019

(65) Prior Publication Data
US 2020/0345541 A1    Nov. 5, 2020

(51) Int. Cl.
*A61F 9/008* (2006.01)
*G01B 9/02* (2006.01)

(52) U.S. Cl.
CPC .......... *A61F 9/008* (2013.01); *G01B 9/02044* (2013.01); *G01B 9/02083* (2013.01); *A61F 2009/00863* (2013.01)

(58) Field of Classification Search
CPC ............ A61F 9/008; A61F 2009/00863; A61F 9/00821; G01B 9/02044; G01B 9/02083; A61B 5/0095; G01N 29/2418
See application file for complete search history.

(56) References Cited

U.S. PATENT DOCUMENTS

| 4,540,283 A | 9/1985 | Bachalo |
| 6,694,173 B1 | 2/2004 | Bende et al. |
| 2004/0039378 A1 | 2/2004 | Lin |
| (Continued) | | |

OTHER PUBLICATIONS

International Search Report and Written Opinion for International Application No. PCT/US2017/063845 dated Feb. 6, 2018, pp. 12.
Gerstman, B.S., "Theoretical modeling of laser-induced explosive pressure generation and vaporization in pigmented cells," Proceedings of the SPIE, Laser-Induced Damage in Optical Materials, vol. 3902, pp. 41-53 (Mar. 3, 2000).
(Continued)

*Primary Examiner* — Gary Jackson
*Assistant Examiner* — Sebastian X Lukjan

(57) ABSTRACT

Technologies are described for monitoring efficacy of laser treatment through cell lysis determination. Current methods for removing diseased tissue may include directing laser treatment toward cells in a treatment area. The laser treatment may induce lysis of the cells without any visual indication of the lysis occurring. According to some examples, a treatment system may direct a pair of laser pulses to cells in a treatment area. The treatment system may derive a first signal and a second signal based on a detected response to the first and second laser pulse within the pair. A signal processor, according to some examples, may determine a difference between the first signal and the second signal and may modify the laser treatment based on the difference.

20 Claims, 12 Drawing Sheets

(56) References Cited

U.S. PATENT DOCUMENTS

| | | | |
|---|---|---|---|
| 2006/0084948 A1* | 4/2006 | Rovati | A61F 9/00821 |
| | | | 606/4 |
| 2010/0292763 A1* | 11/2010 | Brinkmann | A61F 9/008 |
| | | | 607/89 |
| 2011/0238046 A1* | 9/2011 | Dick | A61B 5/0093 |
| | | | 606/5 |
| 2012/0029490 A1* | 2/2012 | Lin | A61F 9/008 |
| | | | 606/4 |
| 2014/0058244 A1* | 2/2014 | Krocak | A61B 5/0095 |
| | | | 600/407 |
| 2014/0176944 A1* | 6/2014 | Addison | A61B 5/0059 |
| | | | 356/400 |
| 2015/0247199 A1 | 9/2015 | Fletcher et al. | |

OTHER PUBLICATIONS

Neumann, J. and Brinkmann, R., "Interferometric noncontact on-line dosimetry control during selective retina treatment (SRT)," Optical Interactions with Tissue and Cells XVI, vol. 5695, Issue 1, pp. 340-347 (Apr. 15, 2005).

Strohm, E.M. and Kolios, M.C., "Classification of blood cells and tumor cells using label-free ultrasound and photoacoustics," Cytometry Part A: Journal of the International Society for Advancement of Cytometry, vol. 87, Issue 8, pp. 741-749 (Aug. 2015).

Strohm, E.M., et al., "Quantitative measurements of apoptotic cell properties using acoustic microscopy," IEEE Transactions on Ultrasonics, Ferroelectrics, and Frequency Control, vol. 57, Issue 10, pp. 2293-2304 (Oct. 2010).

* cited by examiner

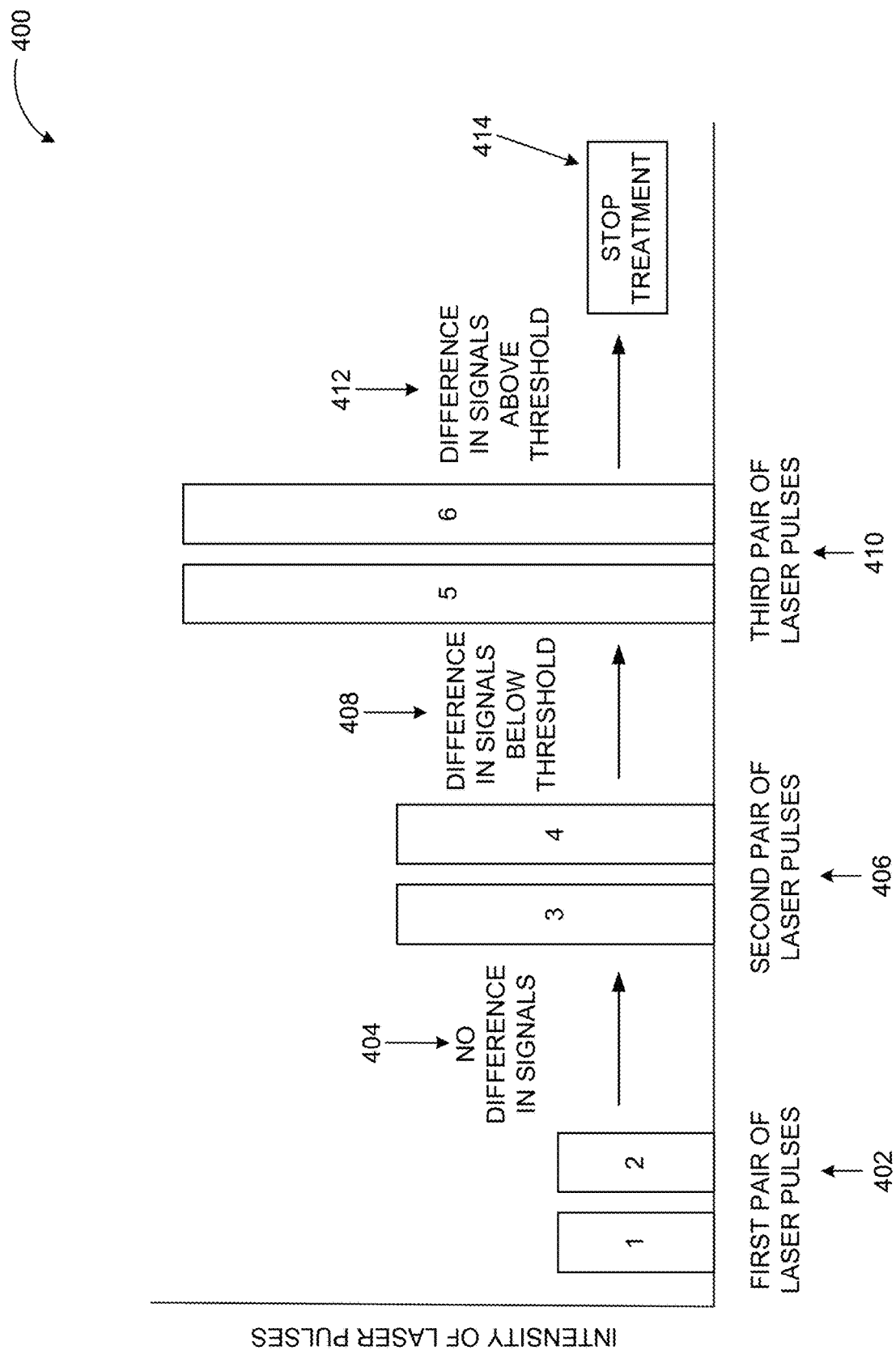

COMPUTER PROGRAM PRODUCT 900

SIGNAL BEARING MEDIUM 902

904 ONE OR MORE INSTRUCTIONS TO:

DIRECT A FIRST LASER PULSE TO A TREATMENT AREA IN AN EYE;
DETECT A FIRST RESPONSE FROM THE EYE;
DERIVE A FIRST SIGNAL BASED ON THE FIRST RESPONSE;
DIRECT A SECOND LASER PULSE TO THE TREATMENT AREA;
DETECT A SECOND RESPONSE FROM THE EYE;
DERIVE A SECOND SIGNAL BASED ON THE SECOND RESPONSE; AND
MODIFY A LASER TREATMENT TO THE EYE BASED ON A DIFFERENCE BETWEEN THE FIRST SIGNAL AND THE SECOND SIGNAL

| COMPUTER-READABLE MEDIUM 906 | RECORDABLE MEDIUM 908 | COMMUNICATIONS MEDIUM 910 |

FIG. 9

MONITOR EFFICACY OF LASER EYE TREATMENT THROUGH CELL LYSIS DETERMINATION

CROSS-REFERENCE TO RELATED APPLICATIONS

The present application is a U.S. National Stage filing under 35 U.S.C. § 371 of International Application PCT/US2017/063845, filed Nov. 30, 2017 and entitled "MONITOR EFFICACY OF LASER EYE TREATMENT THROUGH CELL LYSIS DETERMINATION." The International Application, including any appendices or attachments thereof, is incorporated by reference herein in its entirety.

BACKGROUND

Unless otherwise indicated herein, the materials described in this section are not prior art to the claims in this application and are not admitted to be prior art by inclusion in this section.

Current methods for removing diseased tissue in the eye, such as cells in the retinal pigment epithelium (RPE) that may affected by age-related macular degeneration, may include laser treatment performed by directing laser pulses to cells in an afflicted area. The laser pulses may induce lysis of the cells without any visual indication of the lysis occurring. Failure to determine if cell lysis has occurred may result in over treatment of the area. Over treatment may result in damage to surrounding tissues, which may lead to further complications such as vision loss for example.

Conventional techniques to determine when to stop the laser treatment to prevent such damage may be based on presumed changes in the cells. For example, an intensity of laser pulses directed to the cells in the afflicted area may continuously be increased based on an arbitrarily-set threshold. Because biology inherently has substantial variability, it may be hard to set a threshold effective a priori, and thus such thresholding approaches may risk setting the threshold incorrectly.

SUMMARY

The present disclosure generally describes techniques to monitor efficacy of laser eye treatment through cell lysis determination.

According to some examples, a method to monitor efficacy of a laser treatment to an eye may comprise: directing a first laser pulse to a treatment area in the eye, detecting a first response from the eye, deriving a first signal based on the first response, directing a second laser pulse to the treatment area, detecting a second response from the eye, deriving a second signal based on the second response, and modifying the laser treatment based on a difference between the first signal and the second signal.

According to other examples, a treatment system may be configured to provide and monitor efficacy of a laser treatment to an eye. The treatment system may be comprised of a laser source that may be configured to sequentially emit a first laser pulse and a second laser pulse at an approximately same intensity to a treatment area in an eye. The treatment system may also comprise a detector that may be configured to: detect a first response from the eye following the emission of the first laser pulse, derive a first signal based on the first response, detect a second response from the eye following the emission of the second laser pulse, and derive a second signal based on the second response. The treatment system may further comprise a processor communicatively coupled to the laser source and the detector. The processor may be configured to receive the first signal and the second signal from the detector, determine a difference between the first signal and the second signal, and modify the laser treatment based on whether the difference between the first signal and the second signal is above a particular threshold.

According to further examples, a signal processing apparatus may comprise a communication interface that may be configured to facilitate communication between the signal processing apparatus and a treatment system. The treatment system may be configured to direct a first laser pulse to a treatment area in an eye, detect a first response from the eye, derive a first signal based on the first response, direct a second laser pulse to the treatment area, detect a second response from the eye, and derive a second signal based on the second response. The signal processing apparatus may also comprise a processor coupled to the communication interface and the treatment system. The processor may be configured to: receive, through the communication interface, the first signal and the second signal from the treatment system, determine a difference between the first signal and the second signal, and instruct the treatment system to modify the laser treatment based on a determination whether the difference between the first signal and the second signal is above a particular threshold.

According to some examples, a system may be configured to monitor efficacy of a laser treatment to an eye. The system may comprise a treatment system configured to: direct a first laser pulse to a treatment area in the eye, detect a first response from the eye, derive a first signal based on the first response, direct a second laser pulse to the treatment area, detect a second response from the eye, and derive a second signal based on the second response. The system may also comprise a signal processing apparatus communicatively coupled to the treatment system. The signal processing apparatus may be configured to: receive the first signal and the second signal from the treatment system, determine a difference between the first signal and the second signal, and determine whether the difference between the first signal and the second signal is above a particular threshold. The system may further comprise a controller that may be communicatively coupled to and may be configured to control and coordinate one or more operations of the treatment system and the signal processing apparatus. Responsive to the determination by the signal processing apparatus whether the difference between the first signal and the second signal is above the particular threshold, the controller may be configured to instruct the treatment system to modify the laser treatment.

According to other examples, a method to monitor efficacy of a laser treatment to an area may include directing a first laser pulse to a treatment area, detecting a first response, deriving a first signal based on the first response, directing a second laser pulse to the treatment area, detecting a second response, deriving a second signal based on the second response, and modifying the laser treatment based on a determination whether a difference between the first signal and the second signal is above a particular threshold.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 4 includes a conceptual illustration of modification of a laser treatment to an eye based on signal analysis;

FIG. 9 illustrates a block diagram of an example computer program product, some of which are arranged in accordance with at least some embodiments described herein.

DETAILED DESCRIPTION

Figure 1:
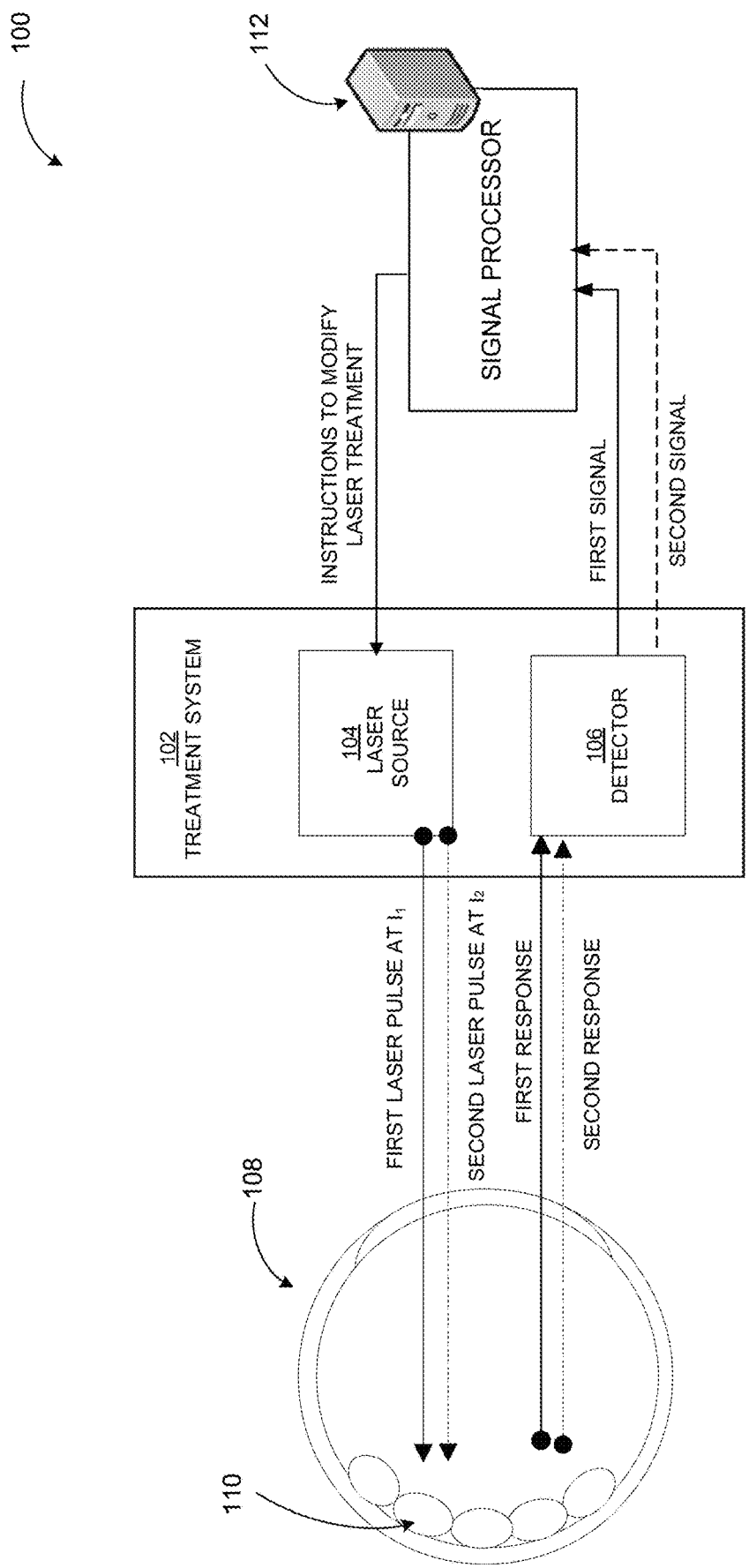
FIG. 1 includes a conceptual illustration of an example method to monitor efficacy of a laser treatment to an eye through cell lysis determination generally.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to monitoring efficacy of laser treatment through determination of cell lysis.

Briefly stated, technologies are generally described to monitor the efficacy of laser treatment through determination of cell lysis. During laser treatment, a treatment system may direct pairwise laser pulses to a group of cells in a treatment area. The treatment system may detect a first response and a second response in the eye after the emission of the first laser pulse and the second laser pulse, respectively. A first signal and a second signal may be derived from the first and second response and may be transmitted to a signal processor. The signal processor may determine a difference between the first signal and the second signal and may determine if the difference is above a particular threshold indicative of lysis of the cells in the treatment area. Based on the determination that the difference is above or below the particular threshold, the signal processor may transmit instructions to the treatment system to modify the laser treatment accordingly. Embodiments as described herein are not limited to the context of an eye undergoing laser treatment. Similar embodiments may be used to monitor other areas of the body undergoing laser treatment, such as the nails or skin, among other examples.

FIG. 1 includes a conceptual illustration of an example method to monitor efficacy of a laser treatment to an eye through cell lysis determination generally, arranged in accordance with at least some embodiments described herein.

As shown in diagram 100, a treatment system 102 may include a laser source 104 and a detector 106 among other components. The laser source 104 may include a semiconductor laser diode, a super-luminescent laser diode, a chemical laser, a gas laser, a solid-state laser, or an optical fiber diode, for example. The detector 106 may be a photodiode, an avalanche photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, or a quantum dot photoconductor, for example. The laser source 104 may direct pairwise laser pulses toward an eye 108 in order to lyse the cells 110 in the treatment area. The direction of the pairwise laser pulses may generate a first response and a second response from the eye 108, respectively. The detector 106 may detect the first response and the second response, and the detector 106 may derive a first signal and a second signal from the respective response.

In an example scenario, the laser source 104 may generate a first laser pulse of a particular intensity ($I_1$) and direct the first laser pulse toward the cells 110 inside of the eye 108. The cells 110 may generate a first response, and the first response may be detected by the detector 106. The cells may expand slightly in response to the first laser pulse, for example. The laser source 104 may generate a second laser pulse of a particular intensity ($I_2$) and direct the second laser pulse toward the cells 110 inside of the eye 108. The cells 110 may generate a second response, and the second response may be detected by the detector 106. Bubbles may form inside the cells 110 in response to the second laser pulse causing the cells 110 to expand further and a pressure wave to form inside the eye 108, for example. The detector 106 may then derive a first signal and a second signal based on the first response and the second response respectively. In some embodiments, while the first laser pulse and the second laser pulse may be therapeutic laser pulses used to treat the cells 110 in the treatment area of the eye 108, the detected first response and second response may be changes in reflection of a light emitting diode (LED).

In one embodiment, the intensity of the first pulse ($I_1$) and intensity of the second pulse ($I_2$) may be approximately the same intensity. The intensity of the first and second pulses may be set as an average intensity level of a response over a pulse length, a peak intensity over the pulse length, a root mean square (RMS) variability of the intensity response over the pulse length, or ratios thereof. In one example, the first pulse and the second pulse may be generated such that they have a smoothed, background-subtracted peak height of ±10% from one another. In another embodiment, the intensity of the first pulse ($I_1$) and intensity of the second pulse ($I_2$) may be distinct and/or variable. The first and second signals derived from the responses to the first and second pulses, respectively, may be normalized by scaling the signals with the incident intensity. For example, through a determination of a ratio of the detected signals to a laser intensity.

The treatment system 102 may transmit the first signal and the second signal to a signal processor 112. The signal processor 112 may be a computing device such as a server, a desktop computer, a mobile computer, a special purpose computing device, or a component level processor, for example. The signal processor 112 may receive the first signal and the second signal from the treatment system 102 and may determine a difference between the signals. The difference may be a ratio of the signals, or the difference may be a change in the signals. The laser treatment may be modified based on the difference between the first signal and the second signal. For example, the signal processor 112 may determine if the difference is above or below a threshold indicating lysis of the cells 110. In other embodiments, a change within the cell other than lysis may be determined, such as photodegradation or photobleaching. If the difference is above the threshold, the signal processor 112 may transmit instructions to the treatment system 102 to cease treatment. If the difference is below the threshold or the difference is unclear based on an error in the detection of the responses or derivation of the signals, among other examples, the signal processor 112 may transmit instructions to the treatment system 102 to direct a subsequent pair of laser pulses in order to repeat the process, where an intensity of the subsequent pair of laser pulses may be adjusted relative to the intensity of the first pulse ($I_1$) and/or the intensity of the second pulse ($I_2$) based on the difference determination. Alternatively, if the difference is below but proximate to the threshold indicating lysis the signal processor 112 may transmit instructions to the treatment system 102 to generate a single laser pulse (e.g., a third laser pulse). An intensity of the third laser pulse may be the same as the intensity of the first pulse ($I_1$) and/or the intensity of the second pulse ($I_2$), or may be adjusted (e.g., increased or decreased) relative to the intensity of the first pulse ($I_1$) and/or the intensity of the second pulse ($I_2$) based on how close the difference is to the threshold.

Continuing the above-described example scenario, the signal processor 112 may receive the first signal and the second signal corresponding with the responses from the first pair of laser pulses. The first signal may correspond to the expansion of the cells 110 in response to the first laser pulse, and the second signal may correspond with the formation of bubbles inside of the cells 110 in response to the second laser pulse. The signal processor 112 may then determine a difference between the first signal and the second signal. In the example scenario, the difference may not be above the threshold indicating lysis because the cells are still intact. In response to the difference being below the threshold indicating lysis, the signal processor 112 may transmit instructions to the treatment system 102 to increase the intensity of a subsequent pair of laser pulses.

In the conceptual diagram 100, the positioning and structure of the treatment system 102, the laser source 104, the detector 106, the eye 108, the cells 110, and the signal processor 112 have been simplified for clarity. Configurations of the apparatus and/or the treatment system 102, the laser source 104, the detector 106, the eye 108, the cells 110, and the signal processor 112 are not limited to the configurations illustrated in the diagram 100.

Additionally, the embodiments are not limited to the specific scenario of laser pulse treatment of cells within the eye discussed in FIG. 1. These embodiments may be incorporated into any technique that involves a direction of a laser pulse to a sample surface followed by a measurement of a response of the sample surface to the laser pulse.

As previously discussed, current methods for removing diseased tissue in the eye may include laser treatment performed by directing laser pulses to cells in the afflicted area. The laser pulses may induce lysis of the cells without any visual indication of the lysis occurring. Failure to determine if cell lysis has occurred may result in over treatment of the area, which may lead to further complications such as vision loss for example. Conventional techniques to determine when to stop the laser treatment to prevent such damage may be based on presumed changes in the cells. For example, an intensity of laser pulses directed to the cells in the afflicted area may continuously be increased based on an arbitrarily-set threshold. Because biology inherently has substantial variability, it may be hard to set a threshold effective a priori, and thus such thresholding approaches may risk setting the threshold incorrectly. In comparison, the embodiments described herein enable determination of an actual change in the cells, not just a presumed change. For example, directing pairwise laser pulses to the cells in the treatment area, detecting a response from the eye to each laser pulse, and comparing the responses may enable determination of an actual change (e.g., lysis) in the cell based on the difference between the signals, where the process may be repeated until an actual change is determined. The proposed approaches may enable an effective response to the variability of biology with accuracy. Therefore, by determining an actual change in the cells versus merely a presumed change in the cells, the embodiments described herein may allow for more reliable monitoring of the efficacy of the laser treatment, which may prevent over treatment and thus may prevent damage to surrounding tissues.

Figure 2A:
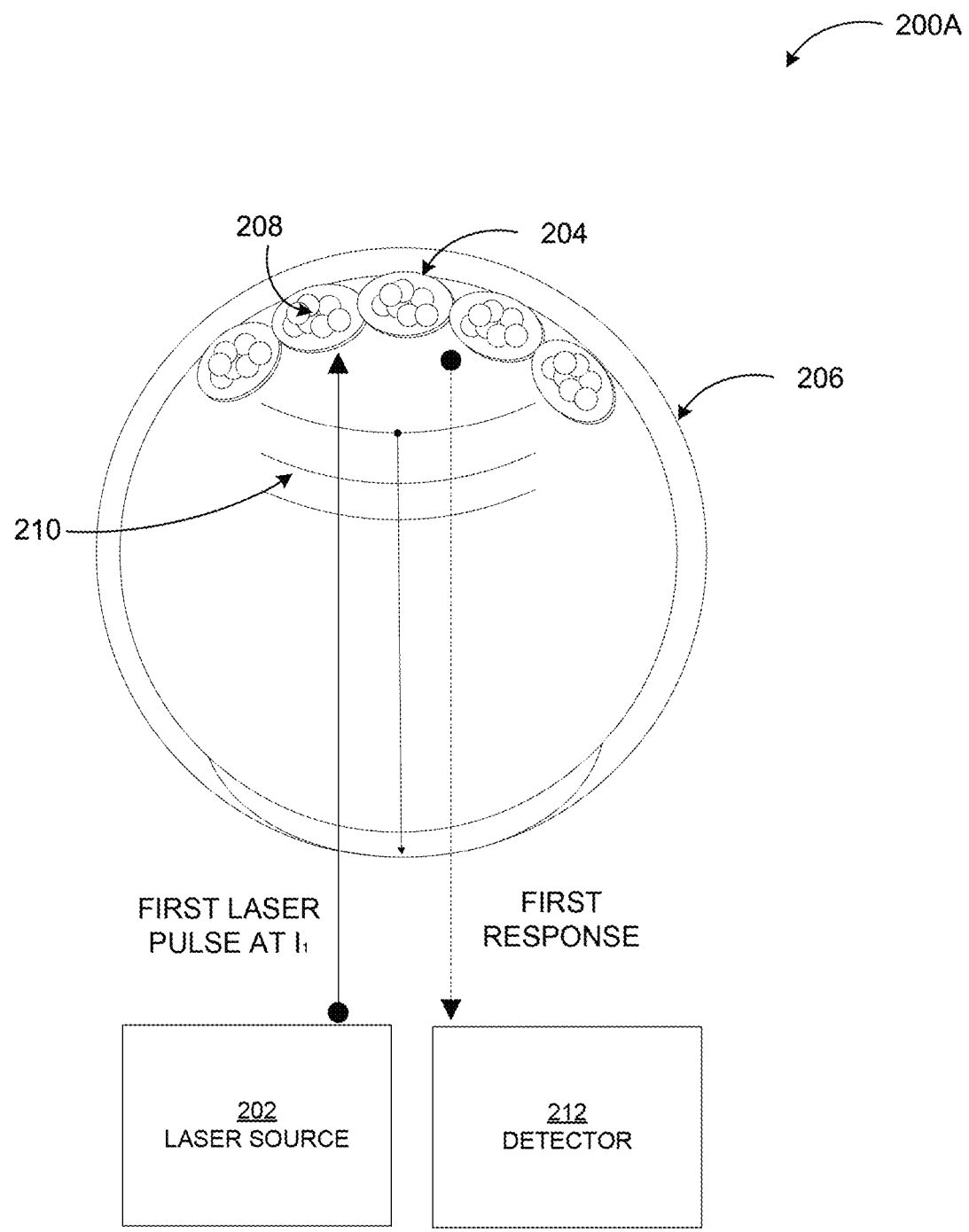
FIGS. 2A and 2B include conceptual illustrations of an example method to determine lysis of a cell within an eye undergoing laser treatment based on a detected change in pressure waves created in response to laser pulses directed to a treatment area of the eye.
Figure 2B:
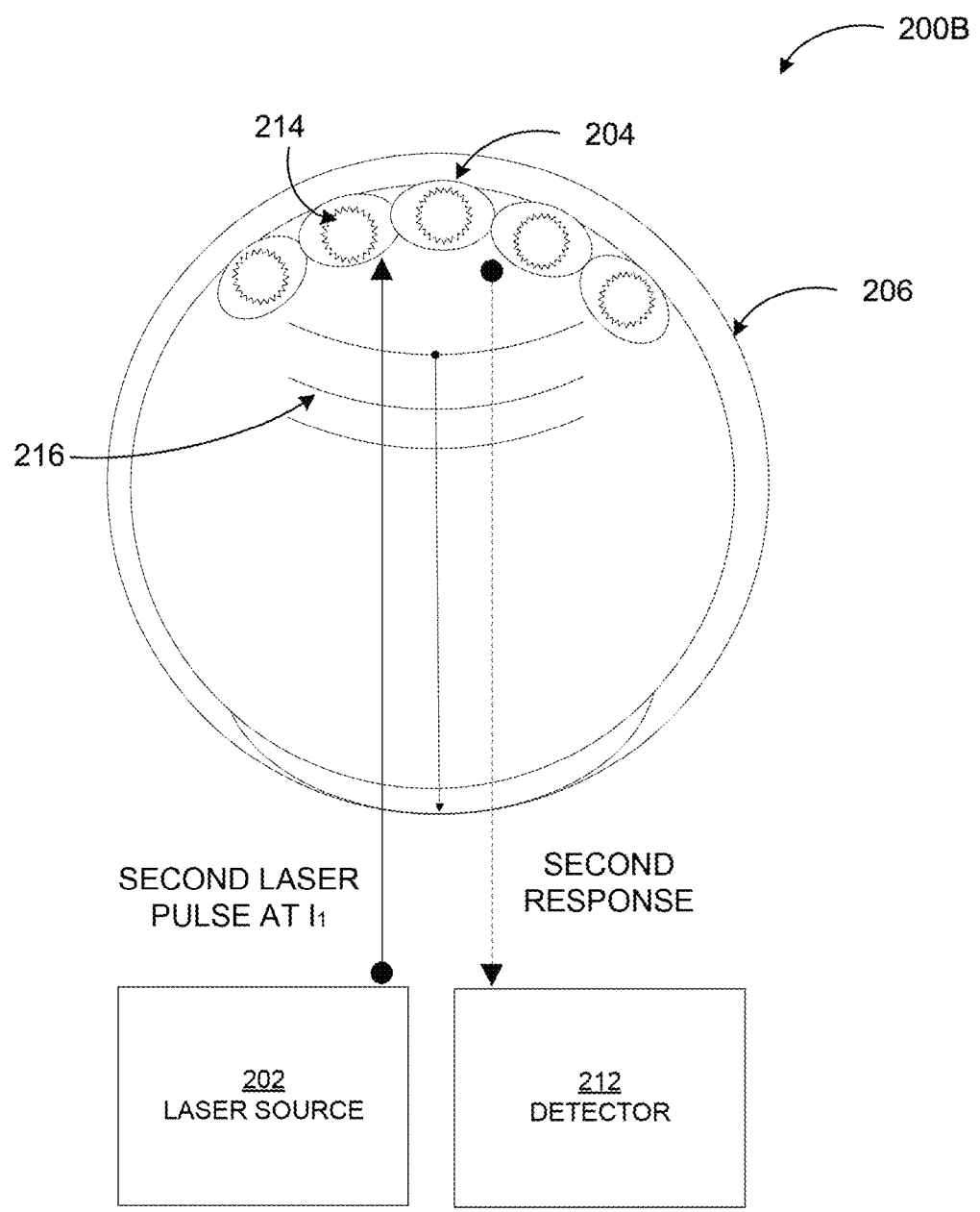

FIGS. 2A and 2B include conceptual illustrations of an example method to determine lysis of a cell within an eye undergoing laser treatment based on a detected change in pressure waves created in response to laser pulses directed to a treatment area of the eye, arranged in accordance with at least some embodiments described herein.

As shown in diagram 200A, a laser source 202 may direct a first laser pulse of a particular intensity ($I_1$) toward a group of cells 204 in an eye 206. The laser source 202 may include a semiconductor laser diode, a super-luminescent laser diode, a chemical laser, a gas laser, a solid-state laser, or an optical fiber diode, for example, and may be a component in a treatment system. In response to the first laser pulse, bubbles 208 may form inside the cells 204 which may cause the cells 204 to expand, and a first pressure wave 210 may be generated inside of the eye 206.

A detector 212 may detect a first response to the first laser pulse in the eye 206. The detector 212 may be a photodiode, an avalanche photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, or a quantum dot photoconductor, for example, and may be a component in a treatment system. In the example scenario, the first pressure wave 210 may interact with the cells 204. The interaction between the first pressure wave 210 and the cells 204 may include an attenuation of the first pressure wave 210 or a shift in frequency of the first pressure wave 210. The interaction may change based on if the cells 204 are intact or if the cells 204 have been lysed. The detector 212 may detect an attenuation of the first pressure wave 210 or a shift in frequency of the first pressure wave 210 after interacting with the cells 204, for example. The detector 212 may detect attenuation or a shift in frequency opto-acoustically by performing photoacoustic spectrometry at an interface external and proximate to the cells 204, such as the interface between the membrane of the cells 204 and the vitreous humor of the eye 206 for example. The detector 212 may then derive a first signal from the first response and may send the first signal to a signal processor.

As shown in diagram 200B, the laser source 202 may direct a second laser pulse of the same intensity ($I_1$) toward the group of cells 204 in the eye 206. In response to the second laser pulse, the bubbles from FIG. 2A may rupture 214 causing the cells 204 to be lysed, and a second pressure wave 216 may be generated. In the example scenario, the detector 212 may detect a change in frequency of or the attenuation of the second pressure wave 216 in a similar manner to the detection of the first response. The detector 212 may derive a second signal from the second response and may send the second signal to the signal processor. The signal processor may determine a difference between the first signal and the second signal and may determine if the difference is above or below a threshold indicating lysis. In the example scenario, the signal processor may determine that the difference between the first signal and the second signal is above the threshold indicating lysis and may transmit instructions to the treatment system to cease treatment.

Figure 3A:
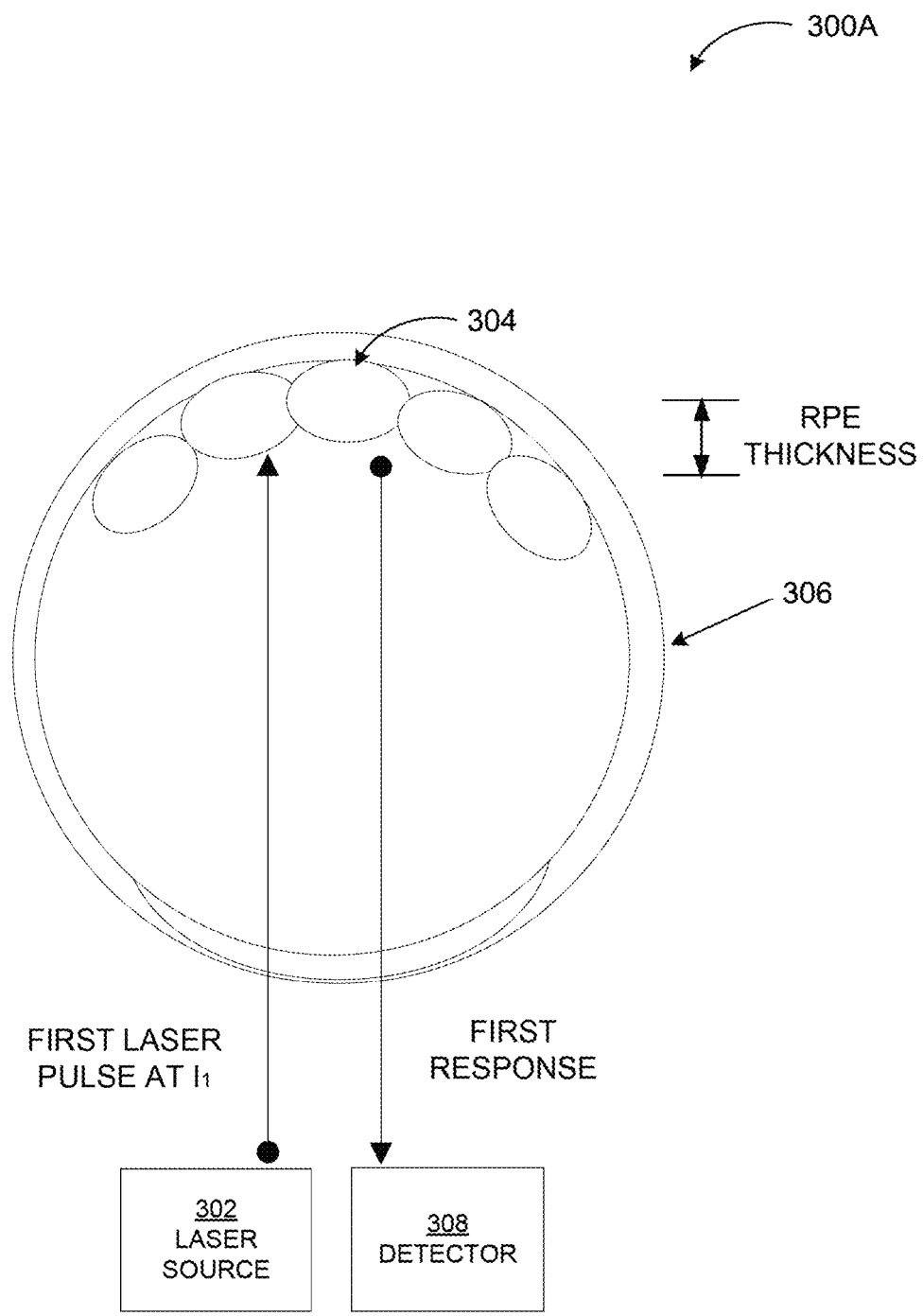
FIGS. 3A-3C include conceptual illustrations of an example method to determine lysis of a cell within an eye undergoing laser treatment based on detected changes in a thickness of a retinal pigment epithelium (RPE) of the eye.
Figure 3B:
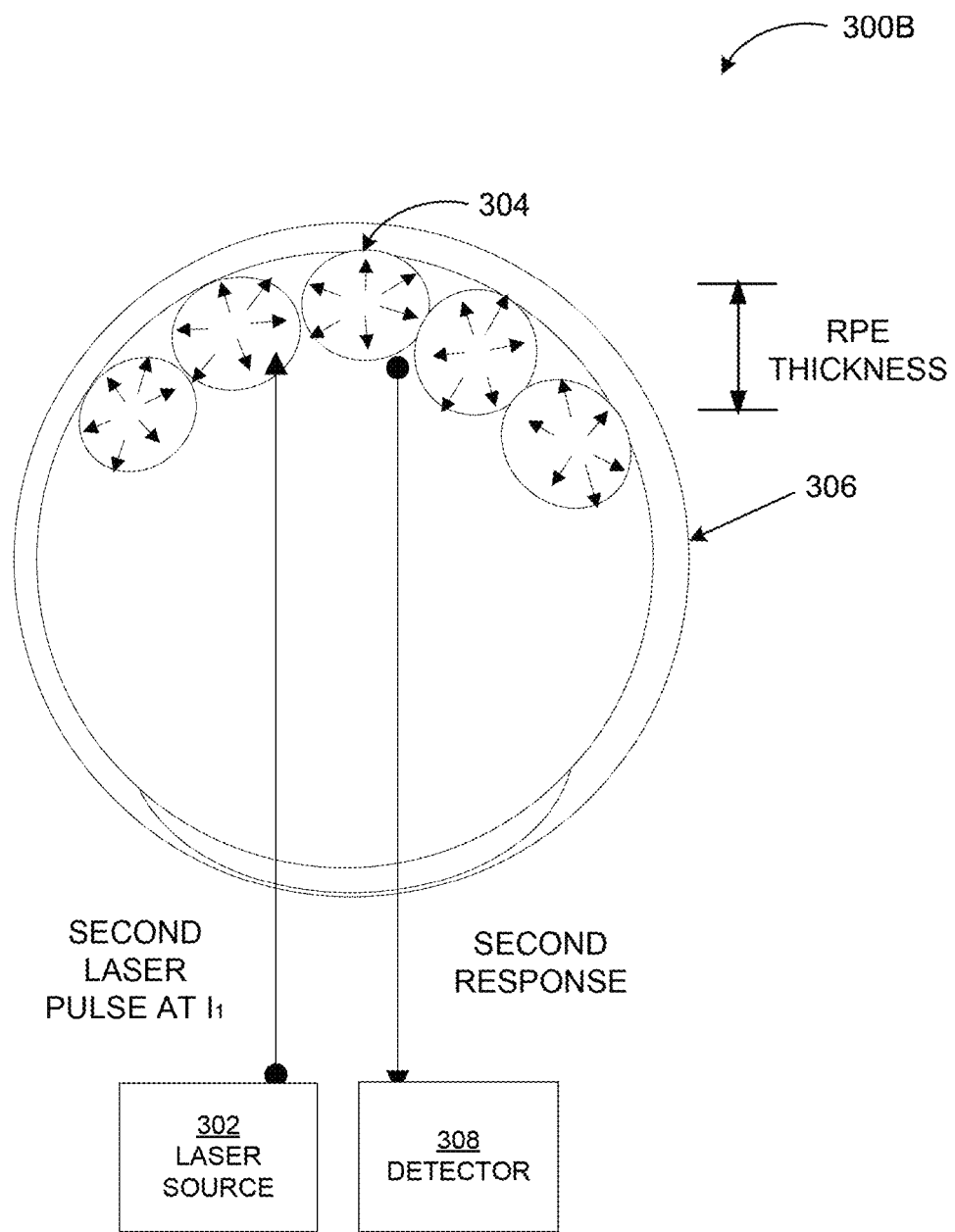
Figure 3C:
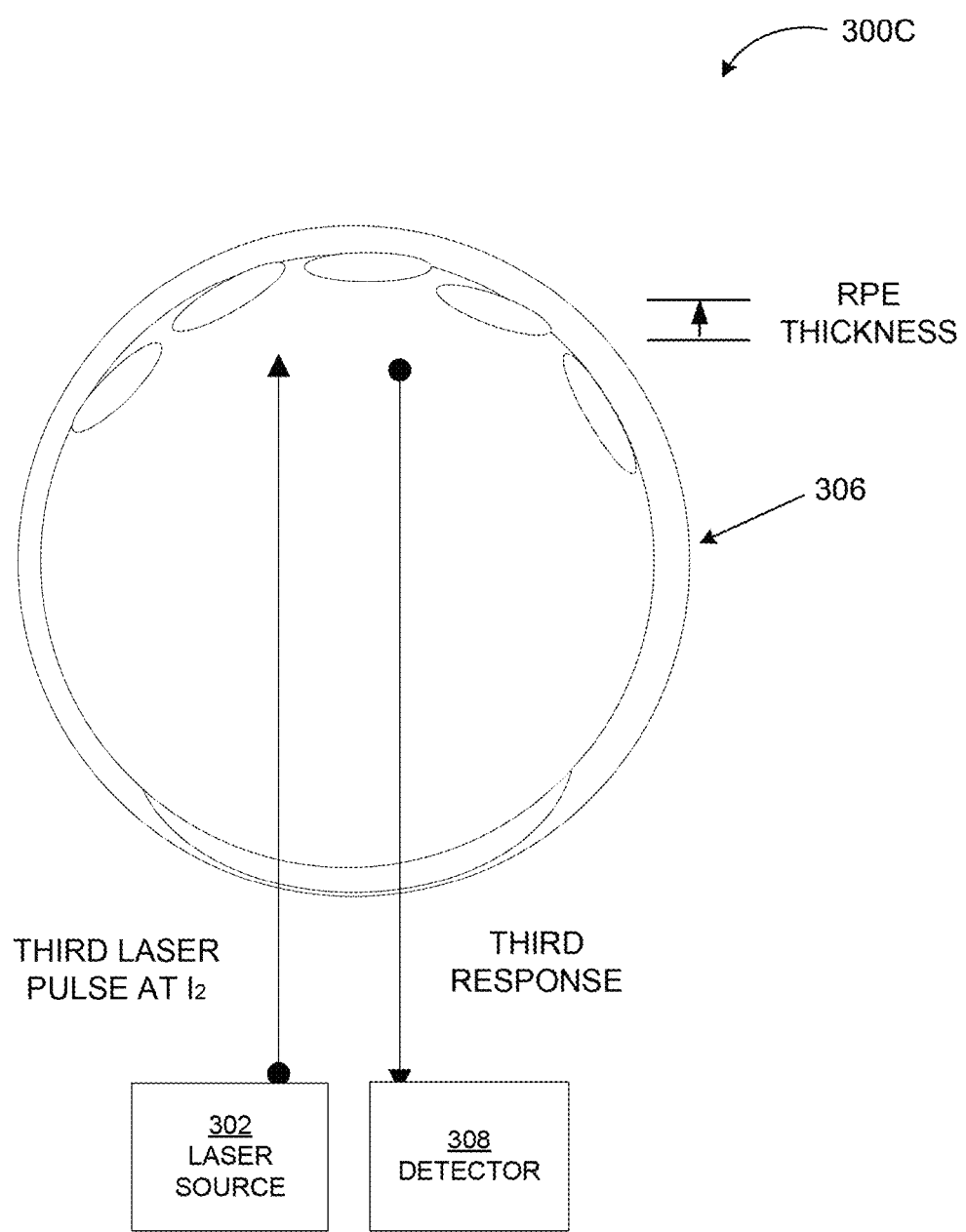

FIGS. 3A-3C include conceptual illustrations of an example method to determine lysis of a cell within an eye undergoing laser treatment based on detected changes in a thickness of a retinal pigment epithelium (RPE) of the eye, arranged in accordance with at least some embodiments described herein.

As shown in diagram 300A, a laser source 302 may direct a first laser pulse of a particular intensity ($I_1$) toward a group of cells 304 in an eye 306. The cells 304 may be a part of the retinal pigment epithelium (RPE) in the eye 306. In response to the first laser pulse, the cells 304 may not undergo any changes, for example. A detector 308 may detect a first response to the first laser pulse in the eye 306. In the example scenario, the detector 308 may use interferometric techniques to measure the thickness of the retinal pigment epithelium after the emission of the first laser pulse. The detector 308 may derive a first signal based the first response and may transmit the first signal to a signal processor.

As shown in diagram 300B, the laser source 302 may direct a second laser pulse of the same intensity ($I_1$) toward the group of cells 304 in the eye 306. In response to the second laser pulse, the cells 304 may expand, which may correspond to an increased thickness of the retinal pigment epithelium (RPE) in the eye 306. The detector may detect a second response to the second laser pulse in the eye 306. In the example scenario, the detector 308 may measure the thickness of the retinal pigment epithelium (RPE) after the emission of the second laser pulse. The detector 308 may derive a second signal from the second response and may transmit the second signal to the signal processor. The signal processor may determine a difference between the first signal and the second signal and whether the difference is above or below a threshold indicating lysis. In the example scenario, the signal processor may determine a difference in thickness of the retinal pigment epithelium (RPE) between the first and second signal. The signal processor may determine that the difference is below but proximate to the threshold indicating lysis, and may send instructions to the laser source 302 to generate a single laser pulse (e.g., a third laser pulse). The instructions may include to adjust an intensity of the third laser pulse relative to the intensity ($I_1$) of the first pulse and second pulse based on the difference determination. For example, the third laser pulse may be adjusted to have an increased intensity ($I_2$).

As shown in diagram 300C, the laser source 302 may direct the third laser pulse of the increased intensity ($I_2$), toward the cells 304, and the detector 308 may detect a third response using similar interferometric techniques to measure the thickness of the retinal pigment epithelium (RPE). In the example scenario, the cells 304 may have been lysed by the third laser pulse of the increased intensity ($I_2$), which may correspond to a substantial decrease in thickness of the retinal pigment epithelium (RPE). The detector 308 may derive a third signal from the third response, and may transmit the third signal to the signal processor. The signal processor may determine, from an analysis of the third signal, a substantial decrease in thickness of the retinal pigment epithelium (RPE) indicating lysis of the cells 304. The signal processor may then send instructions to the laser source 302 to cease treatment.

FIG. 4 includes a conceptual illustration of modification of a laser treatment to an eye based on signal analysis, arranged in accordance with at least some embodiments described herein.

As shown in diagram 400, a treatment system may direct a first pair of laser pulses 402 of a first intensity ($I_1$) toward a group of cells in the eye. The treatment system may detect a first response after emission of the first laser pulse and a second response after emission of the second laser pulse. A first signal and a second signal may be derived from the first response and the second response respectively and may be transmitted to a signal processor. The signal processor may determine a difference between the first signal and the second signal and whether the difference is above a threshold indicating lysis. In the example scenario, the signal processor may determine no difference 404 between the first and second signal and, based on the determination, may send instructions to the treatment system emit a second pair of laser pulses 406 at an increased intensity ($I_2$).

The treatment system may then direct a second pair of laser pulses 406, or the third and fourth laser pulses in the treatment session, at the increased intensity ($I_2$) toward the group of cells in the eye. The treatment system may detect a third response and a fourth response and may derive a third signal and a fourth signal, respectively. The treatment system may transmit the third signal and the fourth signal to the signal processor. In the example scenario, the signal processor may determine the difference between the third signal and the fourth signal is below the threshold 408 indicating lysis. Based on the determination that the difference is below the threshold 408, the signal processor may transmit instructions to the treatment system to emit a third pair of laser pulses 410 at a further increased intensity ($I_3$).

The treatment system may then direct a third pair of laser pulses 410, or the fifth and sixth laser pulses in the treatment session, at the further increased intensity ($I_3$) toward the group of cells in the eye. Similar to the previous laser pulses, the treatment system may detect a fifth and sixth response, derive a fifth and sixth signal from the respective response, and may transmit the fifth and sixth signal to the signal processor. The signal processor may determine that the difference between the fifth signal and the sixth signal is above the threshold indicating lysis 412 and may transmit instructions to cease treatment 414 to the treatment system based on the determination the difference is above the threshold.

Figure 5:
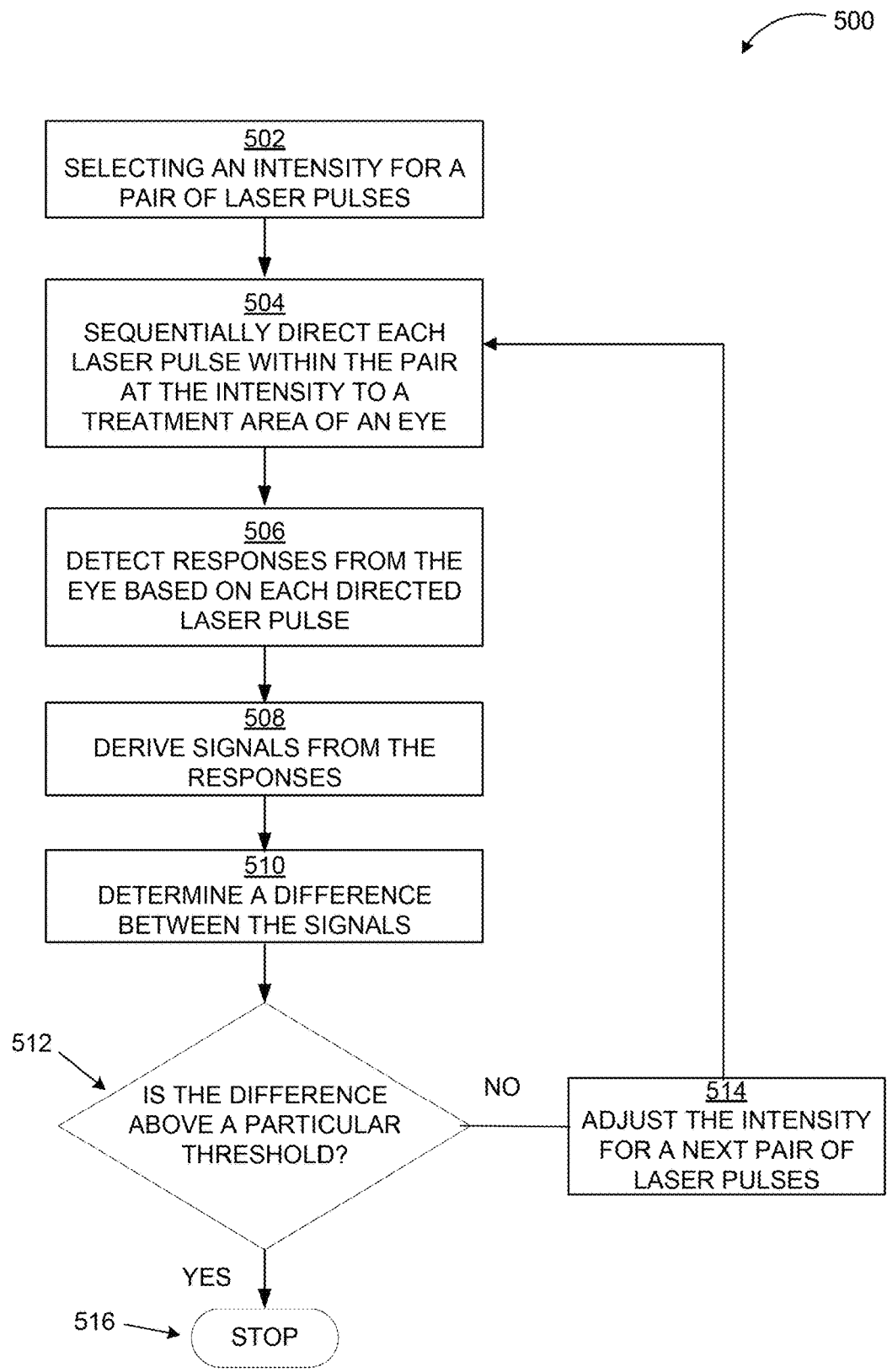
FIG. 5 illustrates an iterative flow process for monitoring efficacy of a laser treatment to an eye through cell lysis determination.

FIG. 5 illustrates an iterative flow process for monitoring efficacy of a laser treatment to an eye through cell lysis determination, arranged in accordance with at least some embodiments described herein.

As shown in diagram 500, an example process to monitor the efficacy of laser treatment through determination of cell lysis may begin with operation 502 where an intensity for a pair of laser pulses, intended to lyse a group of cells in the treatment area, may be selected. The intensity of the laser pulses may be selected based on previous patient data, scientific literature, and factors associated with the current patient (e.g., disease progression, RPE thickness, etc. if known), among other things. The intensity of the first and second pulses may be selected as an average intensity level of a response over a pulse length, a peak intensity over the pulse length, a root mean square (RMS) variability of the intensity response over the pulse length, or ratios thereof. Operation 502 may be followed by operation 504 where the pair of laser pulses is directed at the selected intensity to a treatment area of an eye. The pair of laser pulses may include a first laser pulse and a second laser pulse that are directed sequentially to the treatment area of the eye.

The operation 504 may be followed by or may occur alongside with operation 506 where a response to each laser pulse within the pair of laser pulses may be detected. For example, the first laser pulse may be directed to the treatment area, and a first response may be detected based on the first laser pulse. The second laser pulse may then be directed to the treatment area, and a second response may be detected based on the second laser pulse. Operation 506 may be followed by operation 508 where signals may be derived from the responses. In the example scenario, a first signal may be derived from the first response, and a second signal may be derived from the second response.

Operation 508 may be followed by operation 510 where a difference between the first signal and the second signal may be determined. The difference may be a ratio of the signals, or the difference may be a change in the signals. Operation 510 may be followed by the determination 512 where the difference is determined to be above or below a particular threshold indicating lysis. If the difference is not above the particular threshold, operation 510 may be followed by operation 514 where the intensity of a subsequent pair of laser pulses may be adjusted, such as increasing the intensity for example. The process may begin again starting from operation 504 and may continue until the difference exceeds the threshold. If the difference is above the particular threshold, operation 510 may be followed by operation 516 where the treatment is ceased.

Figure 6:
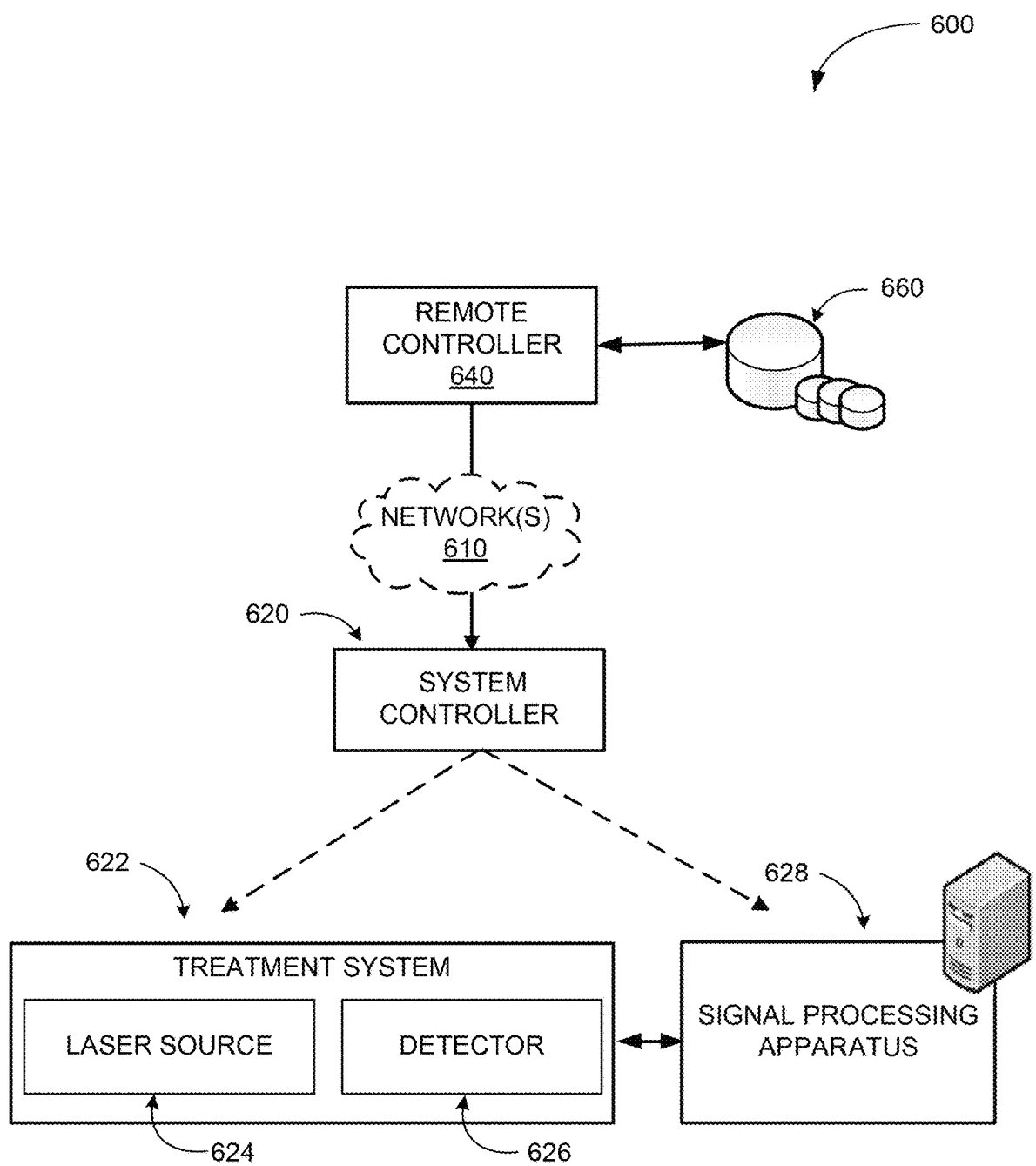
FIG. 6 illustrates major components of an example system configured to monitor efficacy of a laser treatment to an eye through cell lysis determination.

FIG. 6 illustrates major components of an example system configured to monitor efficacy of a laser treatment to an eye through cell lysis determination, arranged in accordance with at least some embodiments described herein.

As shown in diagram 600, a treatment system 622 and the signal processing apparatus 628 may be governed by a system controller 620. The system controller 620 may be managed manually through a variety of inputs, may operate automatically after receiving one or more instructions, or may be operated independently by software. The system controller 620 may also be partially or entirely managed by a remote controller 640, for example, via network 610. The remote controller 640 may be managed manually through a variety of inputs, may operate automatically after receiving one or more instructions, or may be operated independently by software. Data associated with controlling the different processes of monitoring efficacy of laser treatment through cell lysis determination may be stored at and/or received from data stores 660.

The treatment system 622 may include a laser source 624 and a detector 626 in accordance with other embodiments described herein. The laser source 624 may direct a pair of laser pulses to a group of cells in a treatment area of an eye. The detector 626 may detect a first response and a second response after the first laser pulse and the second laser pulse are emitted. The treatment system 622 may derive a first signal and a second signal based on the first response and the second response, respectively. The treatment system 622 may then transmit the first signal and the second signal to the signal processing apparatus 628.

The signal processing apparatus 628 may be a computing device (e.g., a server, a desktop computer, a mobile computer, a special purpose computing device, or even a component level processor) and may receive the first signal and the second signal from the treatment system 622. The signal processing apparatus 628 may determine a difference between the first signal and the second signal and may determine if the difference is above or below a particular threshold indicating lysis. The signal processing apparatus 628 may transmit instructions to the treatment system based on the determination. For example, in response to determining that the difference is above the particular threshold, the signal processing apparatus may send instructions to cease treatment. In another example, responsive to determining that the difference is below the threshold or that there is no difference between the first signal and the second signal, the signal processing apparatus 628 may transmit instructions to increase the intensity of a subsequent pair of laser pulses. In further examples, in response to determining the difference is approximate to the particular threshold, the signal processing apparatus 628 may transmit instructions to send a single pulse to the group of cells in the treatment area.

Figure 7:
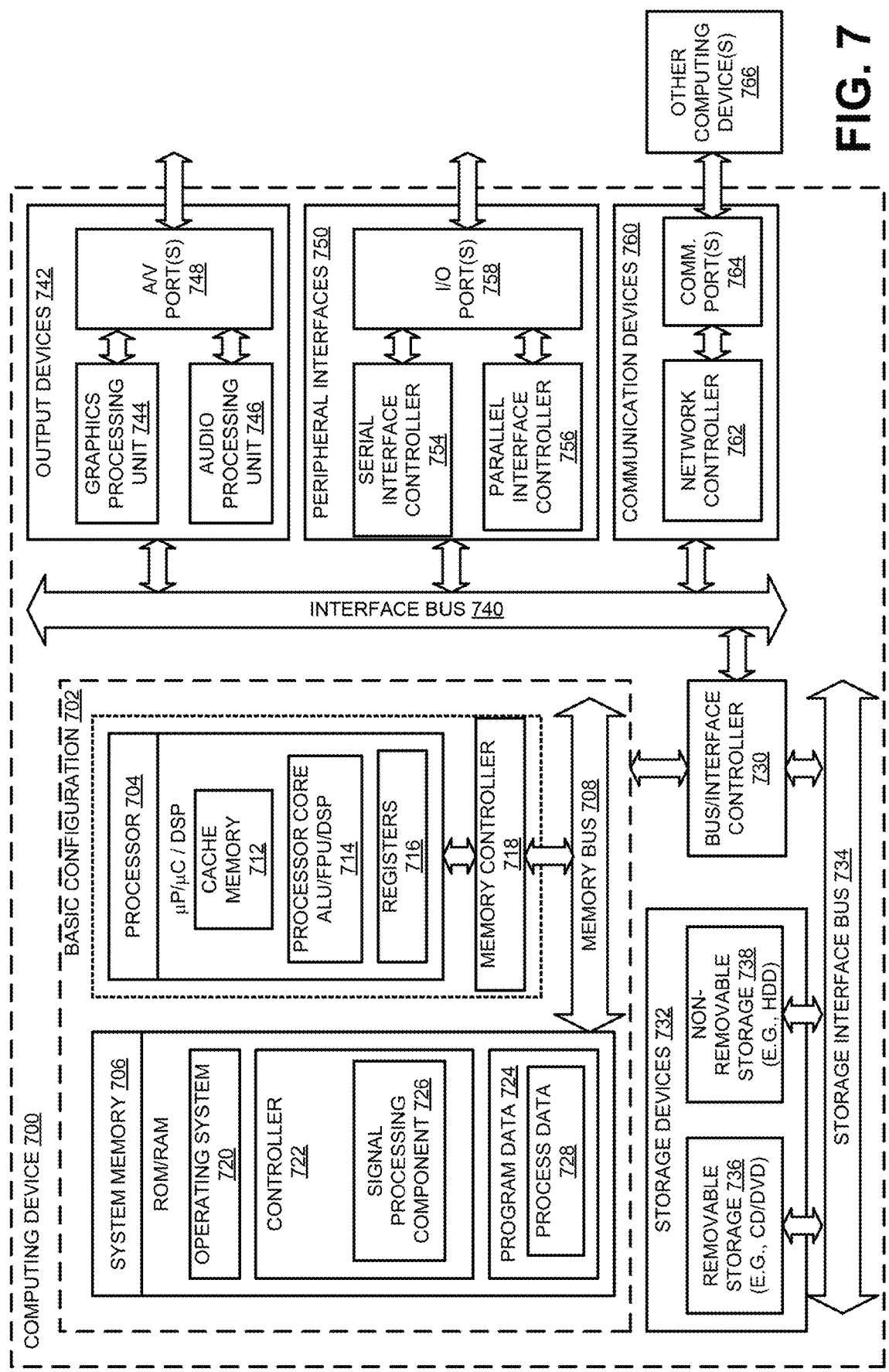
FIG. 7 illustrates a computing device, which may be used in conjunction with a treatment system to modify a laser treatment to an eye based on a cell lysis determination.

FIG. 7 illustrates a computing device, which may be used in conjunction with a treatment system to modify a laser treatment to an eye based on a cell lysis determination, arranged in accordance with at least some embodiments described herein.

In an example basic configuration 702, the computing device 700 may include one or more processors 704 and a system memory 706. A memory bus 708 may be used to communicate between the processor 704 and the system memory 706. The basic configuration 702 is illustrated in FIG. 7 by those components within the inner dashed line.

Depending on the desired configuration, the processor 704 may be of any type, including but not limited to a microprocessor ($\mu$P), a microcontroller ($\mu$C), a digital signal processor (DSP), or any combination thereof. The processor 704 may include one or more levels of caching, such as a cache memory 712, a processor core 714, and registers 716. The example processor core 714 may include an arithmetic logic unit (ALU), a floating point unit (FPU), a digital signal processing core (DSP core), or any combination thereof. An example memory controller 718 may also be used with the processor 704, or in some implementations, the memory controller 718 may be an internal part of the processor 704.

Depending on the desired configuration, the system memory 706 may be of any type including but not limited to volatile memory (such as RAM), non-volatile memory (such as ROM, flash memory, etc.) or any combination thereof. The system memory 706 may include an operating system 720, a controller 722, and program data 724. The controller 722 may include a signal processing component 726. The controller 722 may be configured to transmit instructions to a treatment system based on determinations made by the signal processing component 726. The signal processing component 726 may be configured to receive a first signal and a second signal from the treatment system responsive to a pair of laser pulses directed to the treatment area, respectively. The signal processing component 726 may determine a difference between the first signal and the second signal and may determine if the difference is above a particular threshold indicating lysis. The signal processing component 726 may generate instructions to be transmitted the treatment system based on the determination. The program data 724 may include, among other data, process data 728 or the like, as described herein.

The computing device 700 may have additional features or functionality, and additional interfaces to facilitate communications between the basic configuration 702 and any desired devices and interfaces. For example, a bus/interface controller 730 may be used to facilitate communications between the basic configuration 602 and one or more data storage devices 732 via a storage interface bus 734. The data storage devices 732 may be one or more removable storage devices 6736, one or more non-removable storage devices 738, or a combination thereof. Examples of the removable storage and the non-removable storage devices include magnetic disk devices such as flexible disk drives and hard-disk drives (HDDs), optical disk drives such as compact disc (CD) drives or digital versatile disk (DVD) drives, solid state drives (SSDs), and tape drives to name a few. Example computer storage media may include volatile and nonvolatile, removable and non-removable media implemented in any method or technology for storage of information, such as computer readable instructions, data structures, program modules, or other data.

The system memory 706, the removable storage devices 736 and the non-removable storage devices 738 are examples of computer storage media. Computer storage media includes, but is not limited to, RAM, ROM, EEPROM, flash memory or other memory technology, CD-ROM, digital versatile disks (DVDs), solid state drives (SSDs), or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., one or more output devices 742, one or more peripheral interfaces 750, and one or more communication devices 760) to the basic configuration 702 via the bus/interface controller 730. Some of the example output devices 742 include a graphics processing unit 744 and an audio processing unit 746, which may be configured to communicate to various external devices such as a display or speakers via one or more A/V ports 748. One or more example peripheral interfaces 750 may include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 760 includes a network controller 762, which may be arranged to facilitate communications with one or more other computing devices 766 over a network communication link via one or more communication ports 764. The one or more other computing devices 766 may include servers at a datacenter, customer equipment, and comparable devices.

The network communication link may be one example of a communication media. Communication media may be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 700 may be implemented as a part of a general purpose or specialized server, mainframe, or similar computer that includes any of the above functions. The computing device 700 may also be implemented as a personal computer including both laptop computer and non-laptop computer configurations.

Figure 8:
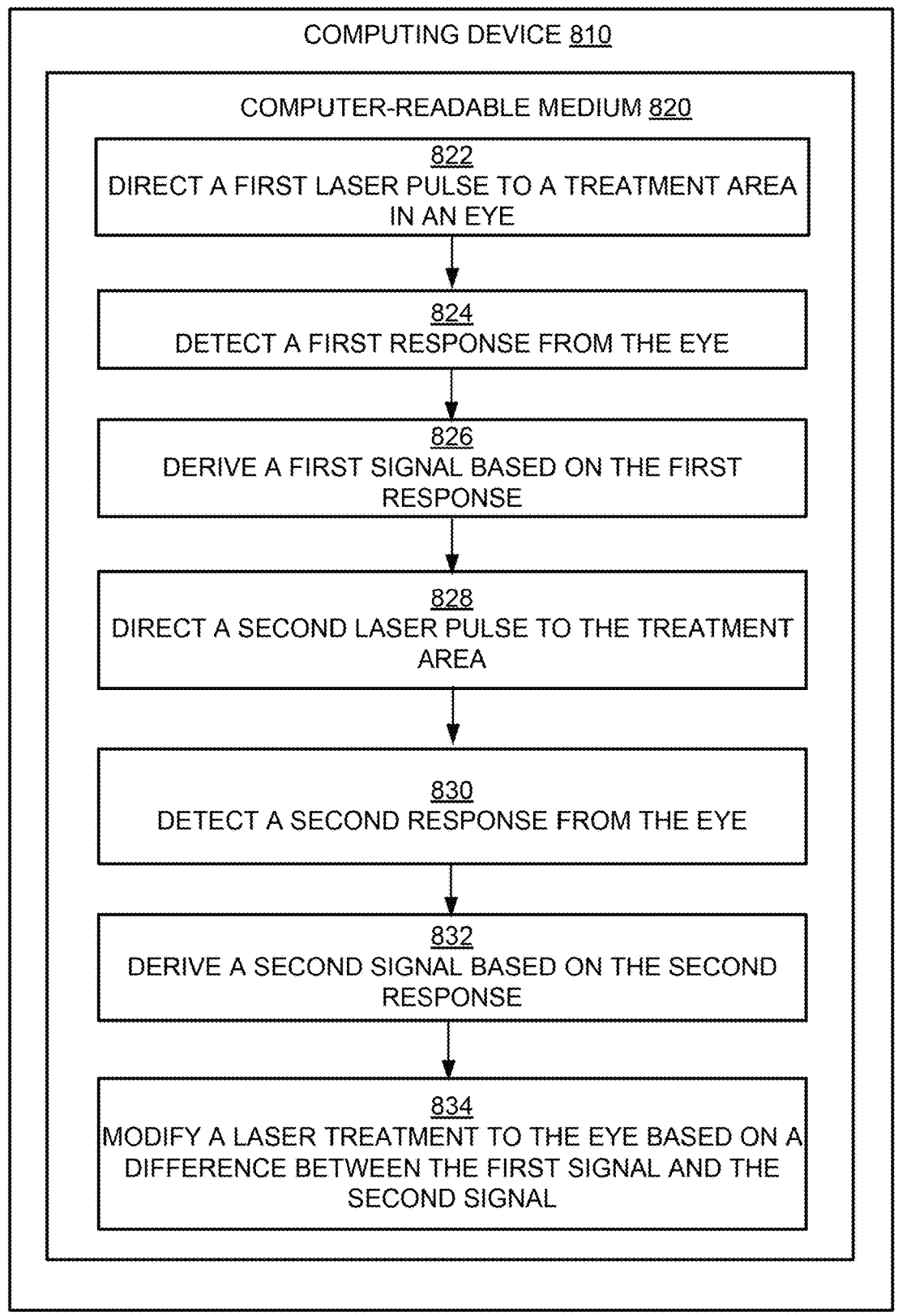
FIG. 8 is a flow diagram illustrating an example method to provide and monitor efficacy of a laser treatment to an eye through cell lysis determination that may be performed by a treatment system in conjunction with a computing device such as the computing device in FIG. 7.

FIG. 8 is a flow diagram illustrating an example method to provide and monitor efficacy of a laser treatment to an eye through cell lysis determination that may be performed by a treatment system in conjunction with a computing device such as the computing device in FIG. 7, arranged in accordance with at least some embodiments described herein.

Example methods may include one or more operations, functions, or actions as illustrated by one or more of blocks 822, 824, 826, 828, 830, 832, and 834 may in some embodiments be performed by a computing device such as the computing device 700 in FIG. 7. Such operations, functions, or actions in FIG. 8 and in the other figures, in some embodiments, may be combined, eliminated, modified, and/or supplemented with other operations, functions or actions, and need not necessarily be performed in the exact sequence as shown. The operations described in the blocks 822-834 may be implemented through execution of computer-executable instructions stored in a computer-readable medium such as a computer-readable medium 820 of a computing device 810.

An example process to monitor the efficacy of laser treatment though cell lysis determination may begin with block 822, "DIRECT A FIRST LASER PULSE TO A TREATMENT AREA IN AN EYE", where a first laser pulse of a particular intensity ($I_1$) may be directed toward a group of cells in a treatment area of an eye.

Block 822 may be followed by block 824, "DETECT A FIRST RESPONSE FROM THE EYE", where a response to the first laser pulse may be detected. For example, the thickness of the retinal pigment epithelium (RPE) may be measured using interferometric techniques after the emission of the first laser pulse. In other examples, a pressure wave may be generated by the first laser pulse, and the pressure wave may undergo a change in frequency or may be attenuated in response to interacting with the cells in the treatment area. The change in frequency or the attenuated may be measured opto-acoustically by performing photoacoustic spectrometry at an interface external and proximate to the cells, such as the interface between the membrane of the cells and the vitreous humor of the eye, for example.

Block 824 may be followed by block 826, "DERIVE A FIRST SIGNAL BASED ON THE FIRST RESPONSE", where a first signal may be derived from the first response in order to be analyzed.

Block 826 may be followed by block 828, "DIRECT A SECOND LASER PULSE TO THE TREATMENT AREA", where a second laser pulse of the same particular intensity ($I_1$) may be directed toward the group of cells in the treatment area.

Block 828 may be followed by block 830, "DETECT A SECOND RESPONSE FROM THE EYE", where a response to the second laser pulse may be detected using the same method used to detect the first response.

Block 830 may be followed by block 832, "DERIVE A SECOND SIGNAL BASED ON THE SECOND RESPONSE", where a second signal may be derived from the second response in order to be analyzed.

Block 832 may be followed by block 834, "MODIFY A LASER TREATMENT TO THE EYE BASED ON A DIFFERENCE BETWEEN THE FIRST AND SECOND SIGNAL", where a difference between the first signal and the second signal is determined. The difference may then be determined to be above or below a particular threshold indicating lysis, and, the laser treatment may be modified accordingly. For example, if the difference is determined to be above the particular threshold indicating lysis, the laser treatment may be ceased. If the difference is determined to be below the particular threshold indicating lysis, at least one additional laser pulse (e.g., a third laser pulse) may be directed to the treatment area of the eye. In some examples, an additional pair of laser pulses (e.g., the third laser pulse and a fourth laser pulse) may be directed to the treatment area of the eye, and the operations described in blocks 822-834 may be repeated. An intensity of the additional laser pulse or pair of laser pulses may be adjusted relative to the intensity of the first and second pulses based on the determination.

The operations included in process 800 are for illustration purposes. Visualization of crowd behavior information for surveillance may be implemented by similar processes with fewer or additional operations, as well as in different order of operations using the principles described herein. The operations described herein may be executed by one or more processors operated on one or more computing devices, one or more processor cores, specialized processing devices, and/or general purpose processors, among other examples.

FIG. 9 illustrates a block diagram of an example computer program product, arranged in accordance with at least some embodiments described herein.

In some examples, as shown in FIG. 9, a computer program product 900 may include a signal bearing medium 902 that may also include one or more machine readable instructions 904 that, in response to execution by, for example, a processor may provide the functionality described herein. Thus, for example, referring to the processor 704 in FIG. 7, the controller 722 may perform or control performance of one or more of the tasks shown in FIG. 9 in response to the instructions 904 conveyed to the processor 704 by the signal bearing medium 902 to perform actions associated with the visualization of crowd behavior information for surveillance as described herein. Some of those instructions may include, for example, direct a first laser pulse to a treatment area in an eye, detect a first response from the eye, derive a first signal based on the first response, direct a second laser pulse to the treatment area, detect a second response from the eye, derive a second signal based on the second response, and modify a laser treatment to the eye based on a difference between the first signal and the second signal, according to some embodiments described herein.

In some implementations, the signal bearing medium 902 depicted in FIG. 9 may encompass computer-readable medium 906, such as, but not limited to, a hard disk drive (HDD), a solid state drive (SSD), a compact disc (CD), a digital versatile disk (DVD), a digital tape, memory, etc. In some implementations, the signal bearing medium 902 may encompass recordable medium 908, such as, but not limited to, memory, read/write (R/W) CDs, R/W DVDs, etc. In some implementations, the signal bearing medium 902 may encompass communications medium 910, such as, but not limited to, a digital and/or an analog communication medium (e.g., a fiber optic cable, a waveguide, a wired communication link, a wireless communication link, etc.). Thus, for example, the computer program product 900 may be conveyed to one or more modules of the processor 704 by an RF signal bearing medium, where the signal bearing medium 902 is conveyed by the communications medium 910 (e.g., a wireless communications medium conforming with the IEEE 802.11 standard).

According to some examples, a method to monitor efficacy of a laser treatment to an eye may comprise: directing a first laser pulse to a treatment area in the eye, detecting a first response from the eye, deriving a first signal based on the first response, directing a second laser pulse to the treatment area, detecting a second response from the eye, deriving a second signal based on the second response, and modifying the laser treatment based on a difference between the first signal and the second signal.

In other examples, detecting the first response and the second response from the eye may comprise opto-acoustically detecting a first pressure wave created in response to the first laser pulse and a second pressure wave created in response to the second laser pulse and performing photoacoustic spectrometry at an interface external and proximate to a retinal pigment epithelium (RPE) of the eye to detect the first pressure wave and the second pressure wave. According to further examples, detecting the first response and the second response from the eye may comprise detecting a first thickness of a retinal pigment epithelium (RPE) of the eye subsequent to the direction of the first laser pulse and a second thickness of the RPE of the eye subsequent to the direction of the second laser pulse and determining the first thickness of the RPE and the second thickness of the RPE using interferometry.

In some examples, modifying the laser treatment based on the difference between the first signal and the second signal may comprise determining whether the difference between the first signal and the second signal is above a particular threshold. The difference between the first signal and the second signal determined to be above the particular threshold may be indicative of a lysis of at least one cell in the treatment area. According to other examples, in response to a determination the difference between the first signal and the second signal is above the particular threshold, modifying the laser treatment may comprise ceasing direction of laser pulses to the treatment area. In further examples, in response to a determination the difference between the first signal and the second signal is below the particular threshold, modifying the laser treatment may comprise directing at least a third laser pulse to the treatment area and adjusting an intensity of the third laser pulse relative to an intensity of the first laser and an intensity of the second laser pulse based on the determination.

In further examples, the intensity of the first laser pulse and the intensity of the second laser pulse may be approximately the same. According to other examples, the method may further comprise detecting a third response from the eye, deriving a third signal based on the third response, directing a fourth laser pulse to the treatment area, detecting a fourth response from the eye, deriving a fourth signal based on the fourth response, and modifying the laser treatment based on a determination of whether a difference between the third signal and the fourth signal is above a particular threshold. In some examples, in response to a determination that the difference between the third signal and the fourth signal is above the particular threshold, modifying the laser treatment may comprise ceasing the direction of laser pulses to the treatment area. In other examples, in response to a determination that the difference between the third signal and the fourth signal is below the particular threshold, modifying the laser treatment may comprise directing a fifth laser pulse to the treatment area, wherein an intensity of the fifth laser pulse is adjusted relative to an intensity of the third laser pulse and the fourth laser pulse based on the determination.

According to some embodiments, a treatment system may be configured to provide and monitor efficacy of a laser treatment to an eye. The treatment system may be comprised of a laser source that may be configured to sequentially emit a first laser pulse and a second laser pulse at an approximately same intensity to a treatment area in an eye. The treatment system may also comprise a detector that may be configured to: detect a first response from the eye following the emission of the first laser pulse, derive a first signal based on the first response, detect a second response from the eye following the emission of the second laser pulse, and derive a second signal based on the second response. The treatment system may further comprise a processor communicatively coupled to the laser source and the detector. The processor may be configured to receive the first signal and the second signal from the detector, determine a difference between the first signal and the second signal, and modify the laser treatment based on whether the difference between the first signal and the second signal is above a particular threshold.

In other embodiments, the laser source may include a semiconductor laser diode, a superluminescent laser diode, a chemical laser, a gas laser, a solid-state laser, or an optical fiber diode. According to further embodiments, the detector may include a photodiode, an avalanche photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, or a quantum dot photoconductor. In some embodiments, the treatment system may be configured to detect a photoacoustic signal from the eye at an interface external and proximate to a retinal pigment epithelium (RPE) of the eye in order to detect a first pressure wave created in response to the first laser pulse and a second pressure wave in response to the second laser pulse.

According to other examples, a method to monitor efficacy of a laser treatment to an area may include directing a first laser pulse to a treatment area, detecting a first response, deriving a first signal based on the first response, directing a second laser pulse to the treatment area, detecting a second response, deriving a second signal based on the second response, and modifying the laser treatment based on a determination whether a difference between the first signal and the second signal is above a particular threshold.

In some embodiments, the processor may be configured to perform interferometry at a retinal pigment epithelium (RPE) of the eye to detect a first thickness and a second thickness of the RPE of the eye subsequent to the emission of the first laser pulse and the second laser pulse, respectively. According to further embodiments, the processor, responsive to a determination that the difference between the first signal and the second signal is above the particular threshold, may be configured to instruct the laser source to cease emission of laser pulses to the treatment area. In other embodiments, the processor, responsive to a determination that the difference between the first signal and the second signal is below the particular threshold, may be configured to instruct the laser source to emit a third laser pulse to the treatment area, and emit a fourth laser pulse to the treatment area. The intensity of the third laser pulse may be adjusted relative to an intensity of the first pulse and an intensity of the second pulse based on the determination.

In other embodiments, the detector may be further configured to detect a third response from the eye following the emission of the third laser pulse, derive a third signal based on the third response, detect a fourth response from the eye following the emission of the fourth laser pulse, and derive a fourth signal based on the fourth response. In further embodiments, the processor may be further configured to receive the third signal and the fourth signal, determine a difference between the third signal and the fourth signal, and modify the laser treatment based on whether the difference between the third signal and the fourth signal is above the particular threshold. According to some embodiments, the processor, responsive to a determination that the difference between the third signal and the fourth signal is above the particular threshold, may be configured to instruct the laser source to cease the direction of laser pulses to the treatment area. In other embodiments, the processor, responsive to a determination, that the difference between the third signal and the fourth signal is below the particular threshold, may be configured to instruct the laser source to emit a fifth laser pulse to the treatment area. In further embodiments, the first laser pulse and the second laser pulse may have an approximately same intensity.

According to some examples, a signal processing apparatus may comprise a communication interface that may be configured to facilitate communication between the signal processing apparatus and a treatment system. The treatment system may be configured to direct a first laser pulse to a treatment area in an eye, detect a first response from the eye, derive a first signal based on the first response, direct a second laser pulse to the treatment area, detect a second response from the eye, and derive a second signal based on the second response. The signal processing apparatus may also comprise a processor coupled to the communication interface and the treatment system. The processor may be configured to: receive, through the communication interface, the first signal and the second signal from the treatment system, determine a difference between the first signal and the second signal, and instruct the treatment system to modify the laser treatment based on a determination whether the difference between the first signal and the second signal is above a particular threshold.

In some examples, the processor may be configured to instruct the treatment system to cease direction of laser pulses to the treatment area responsive to a determination that the difference between the first signal and the second signal is above the particular threshold. In other examples, the processor may be is configured to instruct the treatment system to direct at least a third laser pulse to the treatment area responsive to a determination that the difference between the first signal and the second signal is below the particular threshold. According to further examples, the first laser pulse and the second laser pulse may have an approximately same intensity, and the processor may be further configured to instruct the treatment system to adjust an intensity of the third laser pulse relative to the intensity of the first laser pulse and the second laser pulse based on determination.

In other examples, the processor may be further configured to receive, through the communication interface, a third signal and a fourth signal from the treatment system, determine a difference between the third signal and the fourth signal, and instruct the treatment system to modify the laser treatment based on a determination whether the difference between the third signal and the fourth signal is above the particular threshold. The third signal may be derived based on a third response from the eye detected in response to a direction of the third laser pulse to the treatment area, and the fourth signal may be derived based on a fourth response from the eye detected in response to a direction of a fourth laser pulse to the treatment area.

According to other embodiments, a system may be configured to monitor efficacy of a laser treatment to an eye. The system may comprise a treatment system configured to: direct a first laser pulse to a treatment area in the eye, detect a first response from the eye, derive a first signal based on the first response, direct a second laser pulse to the treatment area, detect a second response from the eye, and derive a second signal based on the second response. The system may also comprise a signal processing apparatus communicatively coupled to the treatment system. The signal processing apparatus may be configured to: receive the first signal and the second signal from the treatment system, determine a difference between the first signal and the second signal, and determine whether the difference between the first signal and the second signal is above a particular threshold. The system may further comprise a controller that may be communicatively coupled to and may be configured to control and coordinate one or more operations of the treatment system and the signal processing apparatus. Responsive to the determination by the signal processing apparatus whether the difference between the first signal and the second signal is above the particular threshold, the controller may be configured to instruct the treatment system to modify the laser treatment.

In some embodiments, the controller may be configured to instruct the treatment system to provide the first signal and the second signal to the signal processing apparatus. In other embodiments, the controller may be configured to instruct the treatment system to cease direction of laser pulses to the treatment area in response to a determination, by the signal processing apparatus, that the difference between the first signal and the second signal is above the particular threshold. According to further embodiments, the controller may be configured to instruct the treatment system to direct at least a third laser pulse to the treatment area in response to a determination, by the signal processing apparatus, that the difference between the first signal and the second signal is below the particular threshold. In some embodiments, the controller may be configured to instruct the treatment system to adjust an intensity of the third laser pulse relative to an intensity of the first laser pulse and an intensity of the second laser pulse based on the determination. In other embodiments, the intensity of the first laser pulse and the intensity of the second laser pulse may be approximately the same.

In other embodiments, the treatment system may be configured to perform photoacoustic spectrometry at an interface external and proximate to a retinal pigment epithelium (RPE) of the eye to detect a first pressure wave created in response to the first laser pulse and a second pressure wave in response to the second laser pulse. In some embodiments, the controller may be configured to perform interferometry at a retinal pigment epithelium (RPE) of the eye to detect a first thickness and a second thickness of the RPE of the eye subsequent to the direction of the first laser pulse and the second laser pulse, respectively.

There are various vehicles by which processes and/or systems and/or other technologies described herein may be effected (e.g., hardware, software, and/or firmware), and the preferred vehicle will vary with the context in which the processes and/or systems and/or other technologies are deployed. For example, if an implementer determines that speed and accuracy are paramount, the implementer may opt for mainly hardware and/or firmware vehicle; if flexibility is paramount, the implementer may opt for mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, t some aspects of the embodiments disclosed herein, in whole or in part, may be equivalently implemented in integrated circuits, as one or more computer programs executing on one or more computers (e.g., as one or more programs executing on one or more computer systems), as one or more programs executing on one or more processors (e.g., as one or more programs executing on one or more microprocessors), as firmware, or as virtually any combination thereof, and that designing the circuitry and/or writing the code for the software and/or firmware are possible in light of this disclosure.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a compact disc (CD), a digital versatile disk (DVD), a digital tape, a computer memory, a solid state drive (SSD), etc.; and a transmission type medium such as a digital and/or an analog communication medium (e.g., a fiber optic cable, a waveguide, a wired communication link, a wireless communication link, etc.).

It is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. A data processing system may include one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A data processing system may be implemented utilizing any suitable commercially available components, such as those found in data computing/communication and/or network computing/communication systems. The herein described subject matter sometimes illustrates different components contained within, or connected with, different other components. Such depicted architectures are merely exemplary, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A method to monitor efficacy of a laser treatment to an eye, the method comprising:
   1) directing a first pair of laser pulses and deriving a pair of signals corresponding to the first pair of laser pulses, respectively, wherein step 1) comprises:

emitting, by the laser source, a first laser pulse of the first pair of laser pulses to a treatment area in the eye;
detecting, by a detector, a first response from the eye;
deriving, by the detector, a first signal of the pair of signals based on the first response;
emitting, by the laser source, a second laser pulse of the first pair of laser pulses to the treatment area;
detecting, by the detector, a second response from the eye; and
deriving, by the detector, a second signal of the pair of signals based on the second response;
2) transmitting, by the detector, the first signal and the second signal to a signal processor;
3) determining, by the signal processor, a difference between the first signal and the second signal; and
4) instructing, by the signal processor, the laser source to control direction of a second pair of laser pulses based on the difference between the first signal and the second signal.

2. The method of claim 1, wherein detecting the first response and the second response from the eye comprises:
opto-acoustically detecting a first pressure wave created in response to the first laser pulse and a second pressure wave created in response to the second laser pulse; and
the method further comprises:
performing photoacoustic spectrometry at an interface external and proximate to a retinal pigment epithelium (RPE) of the eye to detect the first pressure wave and the second pressure wave.

3. The method of claim 1, wherein detecting the first response and the second response from the eye comprises:
detecting a first thickness of a retinal pigment epithelium (RPE) of the eye subsequent to the direction of the first laser pulse and a second thickness of the RPE of the eye subsequent to the direction of the second laser pulse; and
the method further comprises:
determining the first thickness of the RPE and the second thickness of the RPE using interferometry.

4. The method of claim 1, wherein step 4) comprises:
determining whether the difference between the first signal and the second signal is above a particular threshold; and
instructing the laser source to cease the direction of the second pair of laser pulses to the treatment area in response to the difference that is determined to be above the particular threshold.

5. The method of claim 4, wherein step 4) further comprises:
adjusting an intensity of the third laser pulse relative to an intensity of the first laser and an intensity of the second laser pulse based on the determination.

6. The method of claim 5, wherein the intensity of the first laser pulse and the intensity of the second laser pulse are substantially the same.

7. The method of claim 1, wherein step 4) comprises:
determining whether the difference between the first signal and the second signal is above a first particular threshold; and
instructing the laser source to direct the second pair of laser pulses to the treatment area in response to the difference that is determined to be below the first particular threshold, and
wherein the method further comprises:
emitting, by the laser source, a third laser pulse of the second pair of laser pulses to the treatment area in the eye;
detecting, by the detector, a third response from the eye;
deriving, by the detector, a third signal based on the third response;
emitting, by the laser source, a fourth laser pulse of the second pair of laser pulses to the treatment area;
detecting, by the detector, a fourth response from the eye;
deriving, by the detector, a fourth signal based on the fourth response;
transmitting, by the detector, the third signal and the fourth signal to the signal processor;
determining, by the signal processor, a difference between the third signal and the fourth signal; and
instructing, by the signal processor, the laser source to control the direction of laser pulses based on a determination of whether a difference between the third signal and the fourth signal is above a second particular threshold.

8. The method of claim 7, wherein responsive to a determination that the difference between the third signal and the fourth signal is below the second particular threshold, controlling the direction of laser pulses comprises:
directing a third pair of laser pulses to the treatment area or directing a fifth laser pulse to the treatment area, wherein an intensity of the fifth laser pulse is adjusted relative to an intensity of the third laser pulse and the fourth laser pulse based on the determination.

9. A treatment system configured to provide and monitor efficacy of a laser treatment to an eye, the treatment system comprising:
a laser source configured to sequentially emit a first pair of laser pulses including a first laser pulse and a second laser pulse to a treatment area in an eye;
a detector configured to:
detect a first response from the eye following the emission of the first laser pulse;
derive a first signal based on the first response;
detect a second response from the eye following the emission of the second laser pulse; and
derive a second signal based on the second response; and
a processor communicatively coupled to the laser source and the detector, and configured to:
receive the first signal and the second signal from the detector;
determine a difference between the first signal and the second signal; and
instruct the laser source to control the emission of a second pair of laser pulses based on whether the difference between the first signal and the second signal is above a particular threshold.

10. The treatment system of claim 9, wherein
the laser source is one of a semiconductor laser diode, a superluminescent laser diode, a chemical laser, a gas laser, a solid-state laser, and an optical fiber diode; and
the detector is one of a photodiode, an avalanche photodiode, an active-pixel sensor (APS), a Cadmium Zinc Telluride radiation detector, a charge-coupled device (CCD), a Mercury Cadmium Telluride detector, a reverse-biased light emitting diode (LED), a photoresistor, a phototransistor, and a quantum dot photoconductor.

11. The treatment system of claim 9, wherein the treatment system is configured to detect a photoacoustic signal from the eye at an interface external and proximate to a retinal pigment epithelium (RPE) of the eye in order to detect a first pressure wave created in response to the first laser pulse and a second pressure wave in response to the second laser pulse.

12. The treatment system of claim 9, wherein the processor is configured to perform interferometry at a retinal pigment epithelium (RPE) of the eye to detect a first thickness and a second thickness of the RPE of the eye subsequent to the emission of the first laser pulse and the second laser pulse, respectively.

13. The treatment system of claim 9, wherein the processor, responsive to a determination that the difference between the first signal and the second signal is above the particular threshold, is configured to instruct the laser source to:
cease emission of laser pulses to the treatment area; and
wherein the processor, responsive to a determination that the difference between the first signal and the second signal is below the particular threshold, is configured to instruct the laser source to:
emit a third laser pulse or the second pair of laser pulses to the treatment area, wherein an intensity of the third laser pulse is adjusted relative to an intensity of the first pulse and an intensity of the second pulse based on the determination.

14. The treatment system of claim 13, wherein the detector is further configured to:
detect a fourth response from the eye following the emission of a fourth laser pulse of the second pair of laser pulses;
derive a fourth signal based on the fourth response;
detect a fifth response from the eye following the emission of the fifth laser pulse of the second pair of laser pulses; and
derive a fifth signal based on the fifth response.

15. The treatment system of claim 14, wherein the processor is further configured to:
receive the fourth signal and the fifth signal;
determine a difference between the fourth signal and the fifth signal; and
modify instruct the laser source to control direction of laser pulses based on whether the difference between the fourth signal and the fifth signal is above the particular threshold.

16. The treatment system of claim 9, wherein the first laser pulse and the second laser pulse have substantially the same intensity.

17. A signal processing apparatus, comprising:
a communication interface configured to facilitate communication between the signal processing apparatus and a treatment system, wherein the treatment system is configured to emit a first laser pulse of a pair of laser pulses to a treatment area in an eye, detect a first response from the eye, derive a first signal based on the first response, emit a second laser pulse of the pair of laser pulses to the treatment area, detect a second response from the eye, and derive a second signal based on the second response;
a processor coupled to the communication interface and the treatment system, wherein the processor is configured to:
receive, through the communication interface, the first signal and the second signal from the treatment system;
determine a difference between the first signal and the second signal; and
instruct the treatment system to control emission of a next pair of laser pulses based on a determination whether the difference between the first signal and the second signal is above a particular threshold.

18. The signal processing apparatus of claim 17, wherein the processor is configured to instruct the treatment system to emit at least a third laser pulse to the treatment area responsive to a determination that the difference between the first signal and the second signal is below the particular threshold.

19. The signal processing apparatus of claim 18, wherein the first laser pulse and the second laser pulse have substantially the same intensity, and the processor is further configured to instruct the treatment system to adjust an intensity of the third laser pulse relative to the intensity of the first laser pulse and the second laser pulse based on the determination.

20. The signal processing apparatus of claim 18, wherein the processor is further configured to:
receive, through the communication interface, a third signal and a fourth signal from the treatment system, wherein the third signal is derived based on a third response from the eye detected in response to a direction of the third laser pulse to the treatment area and the fourth signal is derived based on a fourth response from the eye detected in response to a direction of a fourth laser pulse to the treatment area;
determine a difference between the third signal and the fourth signal; and
instruct the treatment system to control emission of laser pulses based on a determination whether the difference between the third signal and the fourth signal is above the particular threshold.

* * * * *